(12) United States Patent
Haschke

(10) Patent No.: US 9,192,754 B2
(45) Date of Patent: Nov. 24, 2015

(54) LOW PERMEABILITY SILICONE RUBBER TUBING

(75) Inventor: Erich Guenter Haschke, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 1230 days.

(21) Appl. No.: 13/015,510

(22) Filed: Jan. 27, 2011

(65) Prior Publication Data
US 2012/0192987 A1 Aug. 2, 2012

(51) Int. Cl.
| | |
|---|---|
| F16L 11/00 | (2006.01) |
| F16L 9/14 | (2006.01) |
| A41D 19/00 | (2006.01) |
| B05D 3/00 | (2006.01) |
| B29D 22/00 | (2006.01) |
| B29D 23/00 | (2006.01) |
| B32B 1/08 | (2006.01) |
| B32B 27/08 | (2006.01) |
| B65D 39/00 | (2006.01) |
| A61M 39/08 | (2006.01) |
| F16L 11/04 | (2006.01) |

(52) U.S. Cl.
CPC .......... *A61M 39/08* (2013.01); *F16L 2011/047* (2013.01)

(58) Field of Classification Search
CPC ...... A61M 39/09; A61M 5/142; A61L 29/06; A61L 29/08
USPC ........... 138/137, 140–153; 427/2.3; 428/35.7, 428/36.6–36.8
See application file for complete search history.

(56) References Cited

U.S. PATENT DOCUMENTS

| | | | | |
|---|---|---|---|---|
| 3,927,695 | A | * 12/1975 | Crockwell | ..................... 138/137 |
| 4,101,699 | A | * 7/1978 | Stine et al. | ................. 428/36.91 |
| 4,312,693 | A |   1/1982 | Salensky et al. | |
| 4,347,874 | A |   9/1982 | Sullivan et al. | |
| 4,798,590 | A |   1/1989 | O'Leary et al. | |
| 4,955,899 | A |   9/1990 | Della Corna et al. | |
| 5,147,725 | A | * 9/1992 | Pinchuk | ..................... 428/425.5 |
| 5,152,782 | A |   10/1992 | Kowligi et al. | |
| 5,153,038 | A | * 10/1992 | Koyama et al. | .............. 428/35.8 |
| 5,482,447 | A | * 1/1996 | Sunden et al. | ........... 417/477.12 |
| 5,512,055 | A |   4/1996 | Domb et al. | |
| 5,545,151 | A | * 8/1996 | O'Connor et al. | ............ 604/524 |
| 5,628,774 | A |   5/1997 | Helland et al. | |
| 5,677,007 | A |   10/1997 | Tsai | |

(Continued)

FOREIGN PATENT DOCUMENTS

WO WO 2009001350 A1 * 12/2008

OTHER PUBLICATIONS

Robinson Rubber Products, Rubber Material Selection Guide: AU—Polyester Urethane or Polyether Urethane, 2005, Accessed Jun. 23, 2014 via <http://www.robinsonrubber.com/pdfs/UrethaneRubber.pdf>.*

(Continued)

*Primary Examiner* — Patrick F Brinson
*Assistant Examiner* — Matthew Lembo
(74) *Attorney, Agent, or Firm* — McDermott Will & Emery LLP

(57) ABSTRACT

An IV set is disclosed that includes a silicone rubber tube coated with a layer of a gas barrier material. The coated tube is resilient and has low gas permeability and is suitable for use with peristaltic IV pumps.

13 Claims, 5 Drawing Sheets

(56) References Cited

U.S. PATENT DOCUMENTS

| | | | |
|---|---|---|---|
| 5,888,656 A * | 3/1999 | Suzuki et al. | 428/425.5 |
| 6,558,315 B1 | 5/2003 | Kuyava | |
| 6,673,403 B1 | 1/2004 | Shiiki et al. | |
| 7,078,453 B1 * | 7/2006 | Feeney et al. | 524/493 |
| 7,221,982 B2 | 5/2007 | Aron et al. | |
| 2001/0045238 A1 * | 11/2001 | Genoni et al. | 138/137 |
| 2002/0022825 A1 * | 2/2002 | Saitou et al. | 604/525 |
| 2003/0009151 A1 * | 1/2003 | Wang | 604/526 |
| 2005/0031816 A1 * | 2/2005 | Chang et al. | 428/35.7 |
| 2005/0064210 A1 * | 3/2005 | McGhee et al. | 428/447 |
| 2007/0119511 A1 * | 5/2007 | Donohue et al. | 138/114 |
| 2007/0193642 A1 | 8/2007 | Werner et al. | |
| 2012/0042427 A1 * | 2/2012 | Messier | 2/16 |

OTHER PUBLICATIONS

International Search Report and Written Opinion for PCT/US2012/022805 mailed Aug. 22, 2012 in 7 pages.

* cited by examiner

LOW PERMEABILITY SILICONE RUBBER TUBING

BACKGROUND

1. Field

The present disclosure generally relates to flexible tubing.

2. Description of the Related Art

Many individuals suffer from chronic health problems, the treatment of which requires regular, and sometimes extended, medication deliveries. Certain treatment regimens for diseases such as diabetes, asthma, epilepsy, cancer and even allergies, require the regular delivery of precise amounts of medication for the patient's survival. Treating chronic medical disorders often requires the administration of medication over a long period of time according to a treatment regimen specified by a medical professional, such as a physician.

In cases of patients admitted to a healthcare facility, one or more infusions to be administered to a patient are prescribed by the patient's physician. A pharmacy, generally located within the patient's hospital or healthcare facility, prepares the infusion medication or solution according to the physician's prescription. The pharmacist places the infusion solution in a bag, bottle, syringe, or other container and labels the container. The label typically contains data to identify the patient, physician, medication prescribed, and a control number. The label is generally typed or printed in human readable characters and may also include machine-readable information, such as a bar code that is readable by optical energy or a radio frequency identification (RFID) tag that is readable by radio frequency (RF) energy. The container is transported to the patient's location and a clinician such as a nurse or other health practitioner hangs the container from a rack. The nurse connects a tube between the container and an infusion pumping system and inserts a cannula at the end of the tube into a vein, for an intravenous (IV) infusion, or other part of a patient. The tube may be part of an assembly that includes fittings, connectors, and pumping elements and is frequently referred to as an "IV set." The pump of the infusion pumping system is started and the infusion proceeds.

Existing infusion pumps include peristaltic pumps that sequentially compress and release segments of a flexible line as well as pumps that manipulate pumping chambers that are incorporated into the IV set. The accuracy of a peristaltic pump is affected by the inner diameter of the tube using in the IV set and flexible tubing having a precise inner diameter is more difficult to produce and therefore more expensive. Similarly, the accuracy of an infusion pump that uses a pumping chamber is dependent upon the accuracy of the size and resilience of the pumping chamber, again leading to a need to produce the disposable IV set in quantities of millions with high accuracy.

IV sets used with peristaltic pumps, currently may use polyvinyl chloride (PVC) as the material is both resilient and provides a good gas barrier. One drawback of PVC, however is that it contains di-ethylhexyl phthalate (DEHP) plasticizer, which tends to leach out into the medical fluid, especially for chemotherapy medications such as Taxol and Taxatere. In order to avoid these chemicals leaching into the medical fluid, IV sets currently use silicone rubber as a resilient element, particularly in a pumping segment that is intended to be placed within the IV pump. One drawback of silicone rubber, however, is that it has a relatively high permeability rate of oxygen and nitrogen transfer, thereby presenting a risk of gas migration from the atmosphere through the tube wall and into the medical fluid. This gas transfer may lead to gas bubbles within the medical fluid, which, if transported through the tube and into the bloodstream of a patient, present a hazard to the patient for air embolism. Certain tubes are provided with coatings intended to provide a gas transmission barrier. Current coating materials include parylene, which is sufficiently rigid that it flakes off when the substrate is repeatedly flexed as occurs in a peristaltic IV pump.

SUMMARY

There is a need for a resilient flexible tube for use with a peristaltic IV pump where the tube also has a low rate of gas permeability.

The IV set of the present disclosure provides a pumping element for use in a peristaltic IV pump wherein the pumping element includes a flexible resilient tube that is coated with a gas barrier and therefore has a low permeability rate, reducing the amount of air that is absorbed into the medical fluid. This tube is safer and more effective than the silicone tube alone. Embodiments of the disclosed infusion pump are smaller, more reliable, and quieter than certain existing infusion pumps.

An IV set is disclosed that includes a silicone rubber tube having an outside surface and a layer of a gas barrier material over the outside surface of the silicone rubber tube.

A tube is disclosed that comprises a silicone rubber tube coated on an outside surface with a gas barrier material.

A method of forming a resilient tube having a low permeability is disclosed. The method comprising the steps of applying a layer of a precursor material to an outside surface of a silicone rubber tube, and converting the precursor material to a gas barrier material.

DETAILED DESCRIPTION

The disclosed embodiments of a pumping element, an IV set, and an IV pumping system provide a quiet, reliable method of delivering a fluid at a precise rate using low-cost disposable IV sets.

The method and system disclosed herein are presented in terms of an infusion pump for the delivery of medical fluid to a patient. It will be apparent to those of ordinary skill in the art that the disclosed concepts may be applied to a variety of mechanisms for the pumping of liquids. Nothing in this disclosure should be interpreted, unless specifically stated as such, to limit the application of any method or system disclosed herein to medical applications.

In the following detailed description, numerous specific details are set forth to provide a full understanding of the present disclosure. It will be apparent, however, to one ordinarily skilled in the art that embodiments of the present disclosure may be practiced without some of the specific details.

In other instances, well-known structures and techniques have not been shown in detail so as not to obscure the disclosure.

Figure 1:
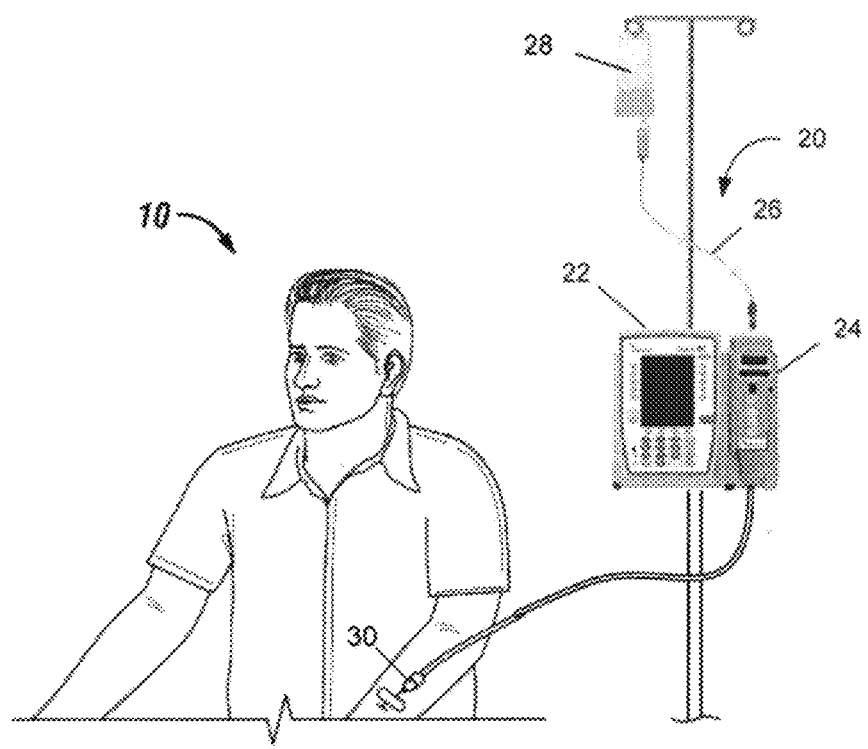
FIG. 1 depicts a patient receiving an infusion of medical fluid administered with a peristaltic IV pump using an IV set according to certain aspects of the disclosure.

FIG. 1 depicts a patient 10 receiving an infusion of medical fluid administered with a peristaltic IV pump 20 using an IV set 26 according to certain aspects of the disclosure. The IV set 26 is coupled at one end to a container 28 of medical fluid, shown as a flexible IV bag in the embodiment of FIG. 1, and coupled to an infusion device 30, such as an IV cannula, at the other end. The IV set 26 includes a pumping segment (not visible in FIG. 1) that is mounted within pumping module 24 of the IV pump 20 that is attached to a controller 22.

Figure 2:
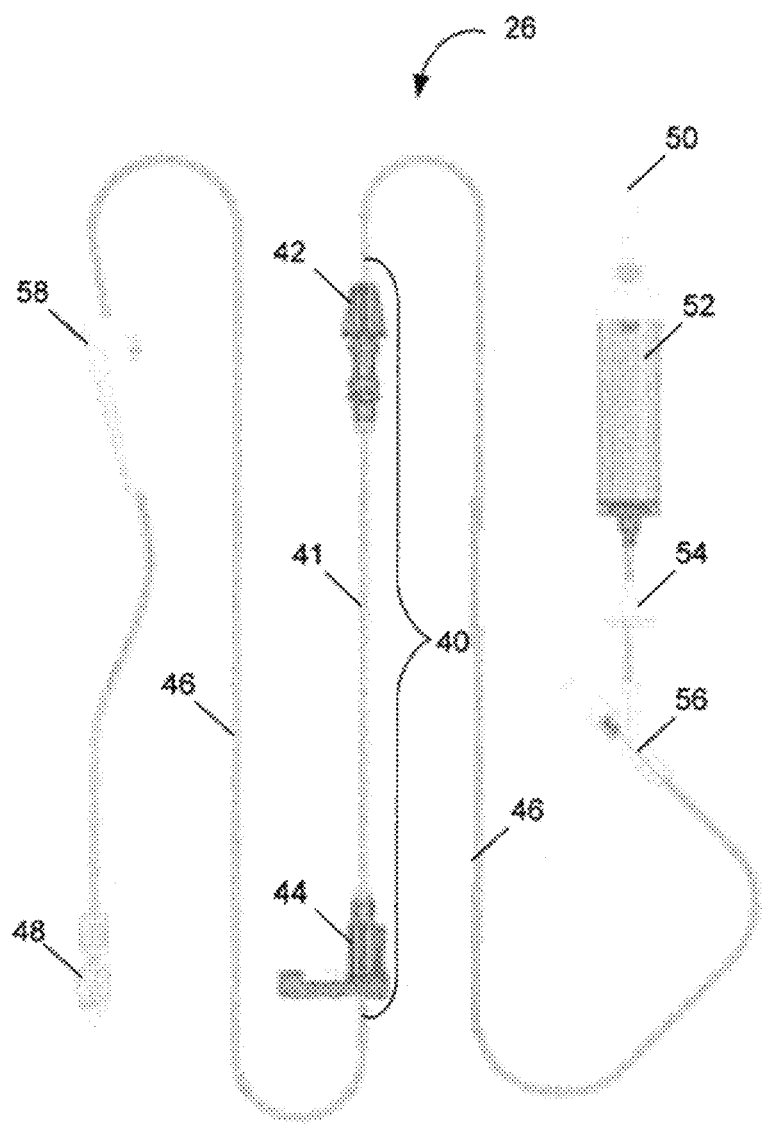
FIG. 2 depicts an IV set comprising a peristaltic pumping segment according to certain aspects of the disclosure.
Figure 4:
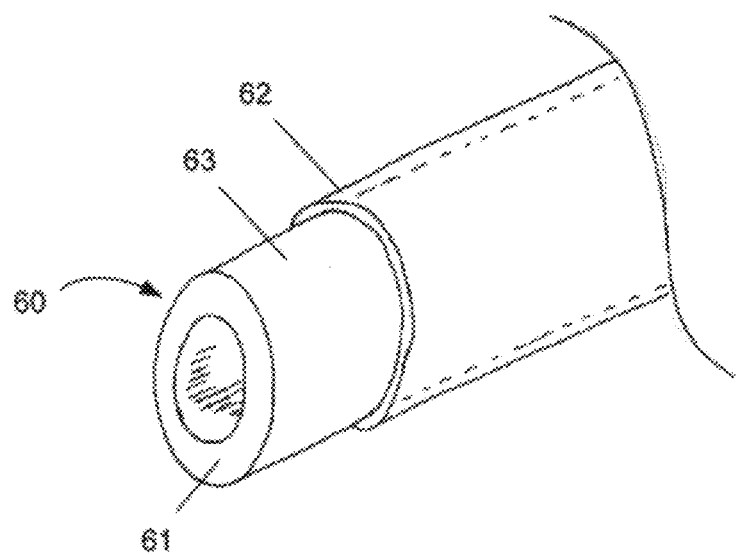
FIG. 4 depicts a tube coated with a gas barrier material according to certain aspects of the disclosure.

FIG. 2 depicts an IV set 26 comprising a peristaltic pumping segment 40 according to certain aspects of the disclosure. The peristaltic pumping segment 40 comprises a length of tube 41 that is suitable for manipulation by the drive elements of a peristaltic IV pump, such as the IV pump 20 of FIG. 1. In this embodiment, pumping segment 40 has a locating fitting 42 at one end and a safety clamp 44 at the other end, both of which fit into receptacles on the IV pump as seen in FIG. 4. The IV set 26 also includes 2 lengths of tube 46 attached to the locating fitting 42 and safety clamp 44, respectively. One length of tube 46 has a connector 48 attached to the other end and a roller clamp 58 present along the length of the tube 46. The second length of tube 46 is attached to a needleless injector port 56, which is then attached to a check valve 54 and a drip chamber 52 and then finally to a connector 50. In this embodiment, connector 50 is a spike adapted to connect to an infusion bag (not shown) such as shown in FIG. 1.

Figure 3:
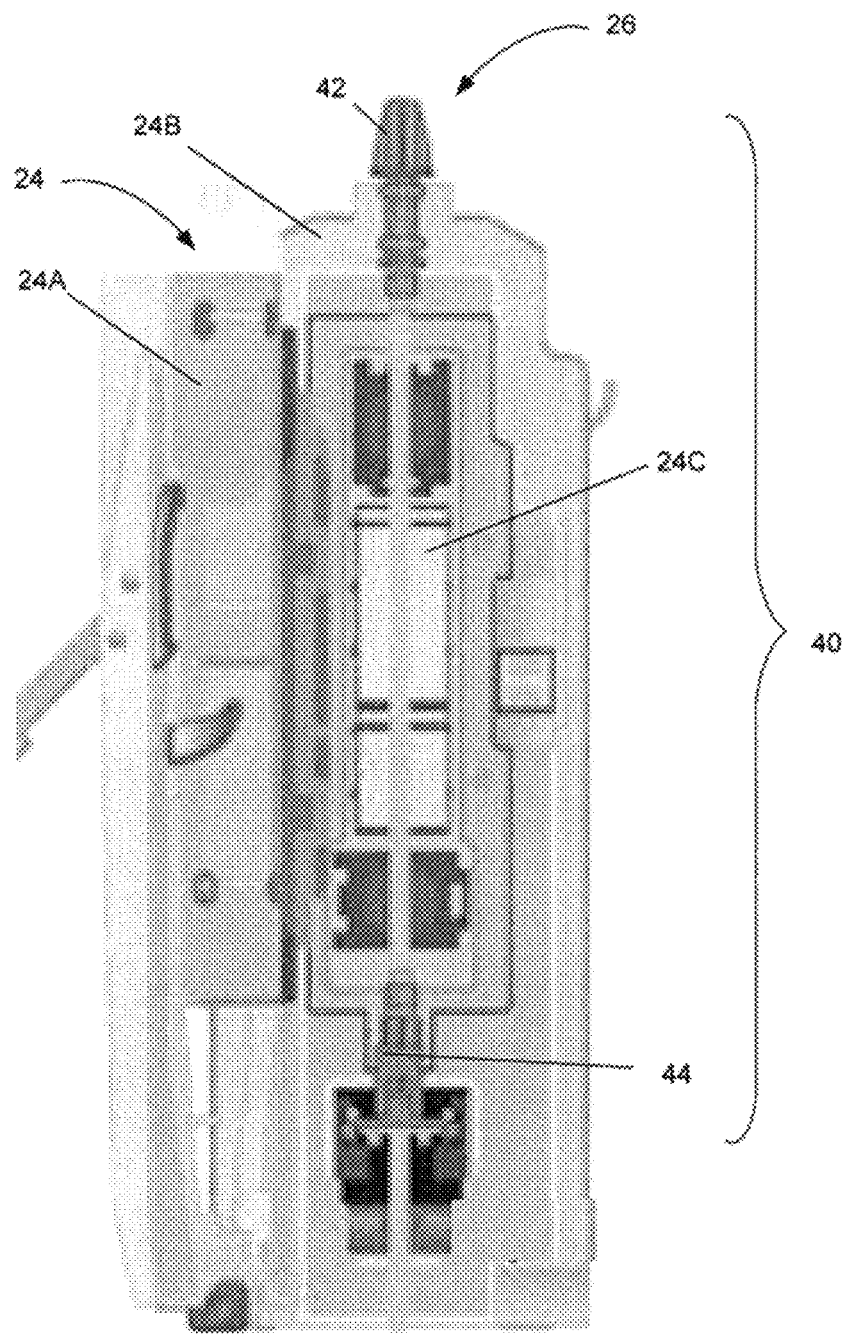
FIG. 3 depicts the peristaltic pumping segment of the IV set of FIG. 2 installed within the pumping element of the IV pump of FIG. 1 according to certain aspects of the disclosure.

FIG. 3 depicts the peristaltic pumping segment of the IV set of FIG. 2 installed within the pumping module 24 of the IV pump 20 of FIG. 1 according to certain aspects of the disclosure. In the view of FIG. 3, the door 24A of the pumping module 24 has been opened and it can be seen that the IV set 26 from FIG. 2 has been installed into body 24B. The locating fitting 42 of IV set 26 is attached to the top of body 24B and the safety clamp 44 has been inserted into a recess at the bottom of 24B. Pumping segment 40 is positioned across the pumping actuator 24C. When door 24A is closed and latched, the pumping module 24 is able to manipulate the tube 41 of peristaltic pumping segment 40 using the pumping actuator 24C to pump fluid in through the locating fitting 42 and out past the safety clamp 44.

FIG. 4 depicts a tube 60 that includes an inner core 61 and a layer 62 of a gas barrier material according to certain aspects of the disclosure. The inner core 61 comprises a silicone, for example silicone rubber, or other material having similar resilience. The inner core 61 has an outer surface 63 over which is located the gas barrier layer 62. The material of gas barrier layer 62 preferentially comprises a urethane, for example thermoplastic polyether-urethane (TPEU) and thermoplastic polyester-polyurethane elastomer (TPAU). In certain embodiments, the gas barrier layer is composed of urethane. The gas barrier layer 62 may be applied by one of the processes of spraying, dipping or extruding, as discussed further with respect to FIG. 5. In certain embodiments, the gas barrier layer 62 is a coating applied to the outer surface 63 of the inner core 61. The thickness of the gas barrier layer 62 is less than 1 millimeter and preferably less than 0.25 millimeter. The specific type of urethane used is preferentially selected or the composition is adjusted by method known to those of ordinary skill in the art to have a hardness that is approximately the same as that of the silicone rubber, preferably within 30 percent of the hardness of the silicone rubber. Materials of this type are typically characterized using Shore A as a testing technique. In other embodiments, the composition of the urethane has been adjusted to have a modulus of elasticity that is within 30 percent of that of the silicone rubber. In certain embodiments, the thickness of the gas barrier material 62 is selected such that the coating of gas barrier material 62 has a permeability rating of less than $1 \times 10^9$ $cm^3 \cdot cm/(cm^2 \cdot s \cdot cmHg)$. In certain embodiments, the gas barrier material may be a material other than urethane that has a permeability rating of less than $1 \times 10^9$ $cm^3 \cdot cm/(cm^2 \cdot s \cdot cmHg)$.

An advantage of the tube 60 of the present disclosure, for example having a layer 62 of urethane over an inner core 61 of silicone rubber, over a pure silicone rubber tube becomes apparent when the permeability rates, as shown in Table 1, of an example pure silicone rubber and example gas barrier materials of TPEU and TPAU that can be employed as the material of gas barrier layer 62 are compared.

TABLE 1

| polymer | nitrogen permeability $\times 10^9$ $cm^3 \cdot cm/$ $(cm^2 \cdot s \cdot cmHg)$ | oxygen permeability $\times 10^9$ $cm^3 \cdot cm/$ $(cm^2 \cdot s \cdot cmHg)$ |
|---|---|---|
| dimethylsilicone rubber | 26.3 | 60.0 |
| TPAU urethane | 0.05 | 0.19 |
| TPEU urethane | 0.05 | 0.16 |

It can be seen that the TPAU urethane has a nitrogen permeability that is over 500× lower than the dimethylsilicone rubber and an oxygen permeability that is over 300× lower than the dimethylsilicone rubber. TPEU urethane has the same relative nitrogen permeability and an oxygen permeability that is approximately 375× lower than the dimethylsilicone rubber. Thus, for example, a 0.1 millimeter coating of TPAU over a tube made of dimethylsilicone rubber with a wall thickness of 1 millimeter produces a composite tube as disclosed herein that has a 30× or better reduction in gas permeability.

As the net gas permeability of a coated tube is a function of multiple parameters, including the thickness of the tubing wall, the thickness of the coating, and the gas permeabilities of the materials from which the tube and coating are formed, it is possible to achieve a desired net gas permeability in a plurality of design configurations. For example, the tube of the previous example, with a dimethylsilicone rubber wall thickness of 1 millimeter and a TPAU coating of 0.1 millimeter, will have approximately the same net permeability as a tube having a dimethylsilicone rubber wall thickness of 5 millimeters and a TPAU coating of 0.0875 millimeter. Similarly, a tube having a dimethylsilicone rubber wall thickness of 1 millimeter and a coating of a material with 2× the permeability of TPAU with a thickness of 0.2 millimeter would also have the same net gas permeability. It can be seen that any gas barrier material having a gas permeability that is less than that of the silicone rubber tube can be used at some thickness to achieve the desired reduction in net gas permeability, although the thickness of the coating increases significantly as the gas permeability of the coating material approaches that of the silicone rubber.

An advantage of using a urethane as a coating or outer layer of a tube for use with a peristaltic IV pump instead of a current gas barrier material such as parylene is the flexibility of the urethane. Parylene is a relatively rigid coating and is currently used to coat rigid substrates such as electronic assemblies to provide a gas and moisture barrier over the electronics. A coating of parylene on a silicone rubber tube cracks and flakes off after a few cycles of compression and expansion of the tube as is experienced in a peristaltic IV pump. The combination of flexibility, strength, and low permeability differentiates urethane from current gas barrier materials.

One method of characterizing a material's hardness is to grade the material using the test method defined in the American Society of Testing Materials (ASTM) standard D2240 according to the A scale, also referred to as the "Shore A" value, which is commonly used for softer plastics. Typical hardnesses of tubing used for peristaltic pumps are commonly in the range of 50-55 Shore A. Parylene, by comparison, is too hard to be measured on the Shore A scale, which has a maximum useful value of approximately 95, and is measured on the Rockwell hardness scale, according to ASTM D785-65, at values of approximately R80. For reference, a Shore A value of 95 can be considered very roughly equivalent to a Rockwell hardness of R55. The relative hardness of parylene to silicone rubber is consistent with the observed tendency of parylene to crack and flake off when used as a coating on a flexible substrate such as silicone rubber. Urethanes, by comparison, can be formulated at a variety of hardnesses that are in the same range of Shore A values as silicone rubber.

Elastomeric materials such as urethane are not commonly characterized by the properties of the modulus of elasticity due to their nonlinear response as they stretch. Instead, the tensile stress required to achieve a specific amount of elongation of a test specimen relative to the original length of the test specimen, using a method defined in an industrial standard such as ASTM D412, is one commonly used parameter to characterize this type of material. Materials are commonly characterized at a number of elongations, such as 20%, 50%, 100%, 200%, and above. For example, the tensile stress at 100% elongation is also known as the "100% Modulus." The choice of which parameter is most useful is dependent upon the application. For the application of tubing used in the pumping segment of a peristaltic pump, elongations of 50-200% may be most useful. The layer of gas barrier material 62 described herein should be of an elasticity similar to or softer than the underlying silicone rubber so as to avoid the problems described above with rigid coating materials.

The coating of gas bather material 62 is not intentionally bonded to the outer surface of tube 60 in certain embodiments. In many current applications of coatings to substrates, attention is focused on creating adhesion between the coating and the substrate. In the present disclosure, while the gas barrier material 62 may have some chemical or mechanical adhesion to the surface of inner core 61, this is neither required nor a problem. As the gas barrier layer 62 is continuous around the inner core 61 of tube 60, the layer 62 is held in place mechanically by the integrity of the layer itself. This is similar to the way in which the coating of insulation is held in place around a copper electrical wire, where the insulation is not intentionally adhered to the wire and is held in place around the wire by the integrity of the insulation material.

Figure 5:
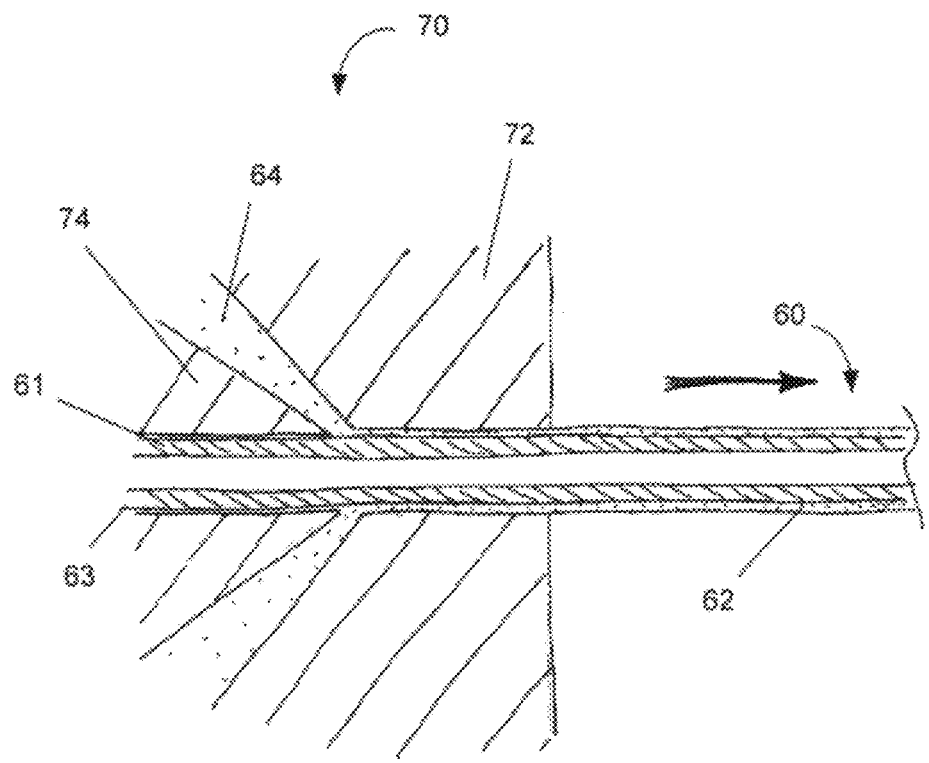
FIG. 5 depicts a tube being coated with a gas barrier material by being pulled through an extrusion die according to certain aspects of the disclosure.

FIG. 5 depicts a tube 60 that is being formed by coating an inner core 61 with a gas bather layer 62. The inner core 61 is pulled through an extruder 70 according to certain aspects of the disclosure. In the embodiment of FIG. 5, the inner core 61 is a thermoset silicone rubber and the gas barrier layer 62 comprises a thermoplastic urethane, where the thermoset silicone rubber has a working temperature that exceeds the melting temperature of the urethane. The extruder 70 includes a die 72 and a die tip 74 behind it that are adjusted so as to provide a path for a melt 64 to be supplied to the surface 63 as the inner core 61 comes through the die tip 74. The clearance between die tip 74 and inner core 61 is very small, such as 100 micrometers, intended to prevent the melt 64 from passing into the space between the die tip 74 and the inner core 61 while allowing the inner core 61 to be drawn through die tip 74 with a minimum of friction. The gap between the die 72 and the inner core 61, however, is sized to create the desired thickness of the gas barrier layer 62. In certain embodiments, the melt 64 is a molten thermoplastic barrier material that hardens by cooling as it exits the die 72. The extrusion process is adjusted according to principals known to those of skill in the art to create a continuous gas barrier layer 62 of the desired and uniform thickness over the inner core 61.

In certain embodiments, the gas barrier material is formed from materials that are not thermoplastics and solidify by other methods. In certain embodiments, the gas barrier layer 62 is created by spraying a liquid precursor over the inner core 61 and allowing the sprayed liquid precursor to cure into the flexible solid gas barrier layer 62. In certain embodiments, the inner core 61 is dipped in a bath of a liquid precursor and then allowed to cure. In certain embodiments, the liquid precursor converts to the flexible solid gas barrier layer 62 by air drying. In certain embodiments, the liquid precursor material is a two-component mixture of liquid that react with each other to form the flexible solid gas barrier layer 62. In certain embodiments, the liquid precursor is cured by exposure to a source of optical radiation, such as ultraviolet (UV) light, which causes the liquid precursor to cure into the flexible solid gas barrier layer 62. In certain embodiments, the liquid precursor material is cured by heating to a temperature above ambient and below the maximum service temperature of the inner core 61.

In summary, the disclosed IV set comprises a flexible, resilient tube having an inner core formed of, for example, a silicone rubber that is coated with a material having low gas permeability, for example a urethane, to provide a pumping segment for use with peristaltic IV pumps. An advantage of silicone rubber over previously used PVC is that silicone rubber does not contain DEHP that leaches into the medical fluids, especially in the presence of chemotherapy drugs such as Taxol and Taxatere. The layer of urethane provides a gas barrier material that reduces the amount of air that passes into the medical fluid and thereby reduces the risk of air bubbles within the IV fluid.

The previous description is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A tube comprising a silicone rubber tube having wall thickness that is from 1 millimeter to 5 millimeter, the silicone rubber tube coated on an outside surface with a gas barrier material, wherein the gas barrier material has an oxygen permeability less than $1 \times 10^9$ cm$^3$·cm / (cm$^2$·s·cmHg), a modulus of elasticity that is within 30% of, and less than, the silicone rubber tube, and a thickness that is from 0.0875 millimeter to 0.1 millimeter.

2. The tube of claim 1, wherein the gas barrier material is a urethane.

3. The tube of claim 2, wherein the has a Shore A hardness less than 100.

4. The tube of claim 2, wherein the has a 100% modulus that is within 50% of the 100% modulus of the silicone rubber.

5. The tube of claim 1, wherein the gas barrier material is not intentionally bonded to the silicone rubber.

6. The tube of claim 1, wherein the gas barrier material has an average thickness of 0.1 millimeter.

7. The tube of claim 1, wherein the gas barrier material is a thermoplastic.

8. An intravenous (IV) set comprising:
silicone rubber tube having an outside surface and a wall thickness that is from 1 millimeter to 5 millimeter; and
a layer of a thermoplastic polyester-polyurethane elastomer gas barrier material covering the outside surface of the silicone rubber tube, the gas barrier material having an oxygen permeability less than $1 \times 10^9$ cm$^3$·cm / (cm$^2$·s·cmHg), a modulus of elasticity that is less than a modulus of elasticity of the silicone rubber tube, and a thickness that is from 0.0875 millimeter to 0.1 millimeter.

9. The IV set of claim 8, wherein the gas barrier material has a Shore A hardness less than 100.

10. The IV set of claim 8, wherein the gas barrier material has a 100% modulus that is within 50% of the 100% modulus of the silicone rubber.

11. The IV set of claim 8, wherein the layer of the gas barrier material is not intentionally bonded to the silicone rubber.

12. The IV set of claim 8, wherein the layer of the gas barrier material has an average thickness of 0.1 millimeter.

13. The IV set of claim 8, wherein the IV set comprises a pumping segment that comprises the silicone rubber tube.

* * * * *